(12) United States Patent
Bertolero (10) Patent No.: US 11,026,567 B2
(45) Date of Patent: Jun. 8, 2021

(54) METHODS AND DEVICES FOR MINIMALLY INVASIVE CARDIAC SURGERY FOR ATRIAL FIBRILLATION

(75) Inventor: Arthur A. Bertolero, Danville, CA (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 13/117,863

(22) Filed: May 27, 2011

(65) Prior Publication Data
US 2011/0230903 A1 Sep. 22, 2011

Related U.S. Application Data

(60) Continuation of application No. 12/273,938, filed on Nov. 19, 2008, now Pat. No. 7,951,069, which is a division of application No. 10/310,675, filed on Dec. 4, 2002, now Pat. No. 7,749,157.

(60) Provisional application No. 60/337,070, filed on Dec. 4, 2001.

(51) Int. Cl.
| | | |
|---|---|---|
| *A61B 1/12* | (2006.01) | |
| *A61B 17/22* | (2006.01) | |
| *A61B 18/14* | (2006.01) | |
| *A61B 5/24* | (2021.01) | |
| *A61B 17/00* | (2006.01) | |
| *A61B 18/00* | (2006.01) | |

(52) U.S. Cl.
CPC .......... *A61B 1/12* (2013.01); *A61B 5/24* (2021.01); *A61B 18/14* (2013.01); *A61B 2017/00243* (2013.01); *A61B 2017/22051* (2013.01); *A61B 2018/00351* (2013.01); *A61B 2018/00982* (2013.01)

(58) Field of Classification Search
USPC .............. 606/139, 142–143, 157–158; 600/114–116
See application file for complete search history.

(56) References Cited

U.S. PATENT DOCUMENTS

| | | | | |
|---|---|---|---|---|
| 3,120,230 A | * | 2/1964 | Skold | 606/158 |
| 3,363,628 A | * | 1/1968 | Wood | 606/158 |
| 3,745,998 A | | 7/1973 | Rose | |
| 3,802,437 A | * | 4/1974 | Kees, Jr. | 606/142 |
| 3,856,016 A | * | 12/1974 | Davis | 128/831 |

(Continued)

OTHER PUBLICATIONS

Borst, Cornelius, et al., "Coronary artery bypass grafting without cardiopulmonary bypass and without interruption of native coronary flow using a novel anastomosis site restraining device ("Octopus")," JACC vol. 27, No. 6, May 1996, pp. 1356-1364.

(Continued)

*Primary Examiner* — Matthew J Kasztejna
(74) *Attorney, Agent, or Firm* — Levine Bagade Han LLP (57) ABSTRACT

Devices for enhancing minimally invasive cardiac surgery include a visualization device including an inflatable balloon at or near the distal end. Some visualization devices also include one or more lumens for allowing the introduction of one or more devices to a surgical site through the visualization device. Systems of the invention involve a visualization device which has at least one lumen for allowing introduction of an ablation device and/or other devices. A visualization device with an inflatable balloon may be positioned to create a space between a heart and pericardium when the balloon is inflated.

19 Claims, 9 Drawing Sheets

(56) References Cited

U.S. PATENT DOCUMENTS

| | | | | |
|---|---|---|---|---|
| 4,224,929 | A | 9/1980 | Furihata | |
| 4,372,316 | A * | 2/1983 | Blake et al. | 606/143 |
| 4,414,721 | A * | 11/1983 | Hufnagel | 606/142 |
| 4,445,892 | A | 5/1984 | Hussein et al. | |
| 4,545,377 | A * | 10/1985 | Cerwin et al. | 606/158 |
| 4,602,632 | A * | 7/1986 | Jorgensen | 606/158 |
| 4,961,738 | A | 10/1990 | Mackin | |
| 4,976,710 | A * | 12/1990 | Mackin | A61B 1/00082 604/916 |
| 4,983,177 | A * | 1/1991 | Wolf | A61B 17/076 606/151 |
| 4,991,578 | A | 2/1991 | Cohen | |
| 5,282,812 | A * | 2/1994 | Suarez, Jr. | 606/158 |
| 5,297,536 | A * | 3/1994 | Wilk | 600/104 |
| 5,306,234 | A * | 4/1994 | Johnson | 128/898 |
| 5,336,252 | A | 8/1994 | Cohen | |
| 5,409,483 | A | 4/1995 | Campbell et al. | |
| 5,423,805 | A | 6/1995 | Brucker et al. | |
| 5,503,617 | A | 4/1996 | Jako | |
| 5,593,405 | A | 1/1997 | Osypka | |
| 5,601,573 | A * | 2/1997 | Fogelberg | A61B 17/1227 227/901 |
| 5,618,307 | A * | 4/1997 | Donlon et al. | 606/205 |
| 5,672,153 | A | 9/1997 | Lax et al. | |
| 5,727,569 | A | 3/1998 | Benetti et al. | |
| 5,782,746 | A | 7/1998 | Wright | |
| 5,807,243 | A | 9/1998 | Vierra et al. | |
| 5,836,311 | A | 11/1998 | Borst et al. | |
| 5,865,730 | A | 2/1999 | Fox et al. | |
| 5,927,284 | A | 7/1999 | Borst et al. | |
| 5,976,132 | A | 11/1999 | Morris | |
| 6,013,027 | A | 1/2000 | Khan et al. | |
| 6,015,378 | A | 1/2000 | Borst et al. | |
| 6,036,641 | A | 3/2000 | Taylor et al. | |
| 6,036,685 | A | 3/2000 | Mueller | |
| 6,039,733 | A | 3/2000 | Buysse et al. | |
| 6,086,586 | A | 7/2000 | Hooven | |
| 6,110,106 | A | 8/2000 | MacKinnon et al. | |
| 6,161,543 | A | 12/2000 | Cox et al. | |
| 6,237,605 | B1 | 5/2001 | Vaska et al. | |
| 6,251,065 | B1 | 6/2001 | Kochamba et al. | |
| 6,277,065 | B1 | 8/2001 | Donofrio | |
| 6,309,349 | B1 | 10/2001 | Bertolero et al. | |
| 6,328,688 | B1 | 12/2001 | Borst et al. | |
| 6,334,843 | B1 | 1/2002 | Borst et al. | |
| 6,336,898 | B1 | 1/2002 | Borst et al. | |
| 6,338,712 | B2 | 1/2002 | Spence et al. | |
| 6,338,738 | B1 | 1/2002 | Bellotti et al. | |
| 6,346,077 | B1 | 2/2002 | Taylor et al. | |
| 6,350,229 | B1 | 2/2002 | Borst et al. | |
| 6,352,534 | B1 | 3/2002 | Paddock et al. | |
| 6,364,826 | B1 | 4/2002 | Borst et al. | |
| 6,371,906 | B1 | 4/2002 | Borst et al. | |
| 6,390,976 | B1 | 5/2002 | Spence et al. | |
| 6,394,948 | B1 | 5/2002 | Borst et al. | |
| 6,463,332 | B1 | 10/2002 | Aldrich | |
| 6,464,630 | B1 | 10/2002 | Borst et al. | |
| 6,482,151 | B1 | 11/2002 | Vierra et al. | |
| 6,484,727 | B1 | 11/2002 | Vaska et al. | |
| 6,488,689 | B1 * | 12/2002 | Kaplan et al. | 606/139 |
| 6,511,416 | B1 | 1/2003 | Green, II et al. | |
| 6,514,250 | B1 | 2/2003 | Jahns et al. | |
| 6,522,905 | B2 | 2/2003 | Desai | |
| 6,524,338 | B1 | 2/2003 | Gundry | |
| 6,527,767 | B2 | 3/2003 | Wang et al. | |
| 6,544,263 | B2 | 4/2003 | Morgan et al. | |
| 6,595,989 | B1 | 7/2003 | Schaer | |
| 6,599,237 | B1 | 7/2003 | Singh | |
| 6,610,073 | B1 * | 8/2003 | Levinson | A61B 17/122 606/151 |
| 6,645,202 | B1 | 11/2003 | Pless et al. | |
| 6,652,518 | B2 | 11/2003 | Wellman et al. | |
| 6,659,939 | B2 * | 12/2003 | Moll et al. | 600/102 |
| 6,758,809 | B2 | 7/2004 | Briscoe et al. | |
| 6,830,174 | B2 * | 12/2004 | Hillstead et al. | 227/175.1 |
| 6,849,075 | B2 | 2/2005 | Bertolero et al. | |
| 6,890,295 | B2 | 5/2005 | Michels et al. | |
| 7,018,328 | B2 | 3/2006 | Mager et al. | |
| 7,226,448 | B2 | 6/2007 | Bertolero et al. | |
| 7,237,555 | B2 | 7/2007 | Kochamba et al. | |
| 7,338,434 | B1 | 3/2008 | Haarstad et al. | |
| 7,542,807 | B2 | 6/2009 | Bertolero et al. | |
| 7,594,915 | B2 | 9/2009 | Kochamba et al. | |
| 7,682,305 | B2 | 3/2010 | Bertolero et al. | |
| 7,749,157 | B2 | 7/2010 | Bertolero | |
| 7,819,867 | B2 | 10/2010 | Bertolero et al. | |
| 7,951,069 | B2 | 5/2011 | Bertolero | |
| 2002/0026094 | A1 | 2/2002 | Roth | |
| 2002/0056460 | A1 | 5/2002 | Boyd | |
| 2002/0068855 | A1 | 6/2002 | Daniel et al. | |
| 2002/0099270 | A1 | 7/2002 | Taylor et al. | |
| 2002/0099390 | A1 | 7/2002 | Kaplan | |
| 2002/0177846 | A1 | 11/2002 | Mulier et al. | |
| 2003/0009080 | A1 | 1/2003 | Peng et al. | |
| 2003/0010346 | A1 | 1/2003 | Paolitto et al. | |
| 2003/0060685 | A1 | 3/2003 | Houser et al. | |
| 2003/0158463 | A1 | 8/2003 | Julian et al. | |
| 2003/0158464 | A1 | 8/2003 | Bertolero | |
| 2005/0010179 | A1 | 1/2005 | Bertolero et al. | |
| 2005/0119653 | A1 | 6/2005 | Swanson | |
| 2005/0119654 | A1 | 6/2005 | Swanson et al. | |
| 2005/0240175 | A1 | 10/2005 | Bertolero et al. | |
| 2006/0015165 | A1 | 1/2006 | Bertolero et al. | |
| 2006/0155272 | A1 | 7/2006 | Swanson | |
| 2007/0233226 | A1 | 10/2007 | Kochamba et al. | |
| 2008/0294154 | A1 | 11/2008 | Ibrahim et al. | |
| 2009/0048591 | A1 | 2/2009 | Ibrahim et al. | |
| 2009/0076501 | A1 | 3/2009 | Bertolero et al. | |
| 2009/0076537 | A1 | 3/2009 | Bertolero | |
| 2009/0163768 | A1 | 6/2009 | Ibrahim et al. | |
| 2009/0281541 | A1 | 11/2009 | Ibrahim et al. | |

OTHER PUBLICATIONS

Jansen, Erik, et al., "Less Invasive off-pump CABG using a suction device for immobilization: The Octopus method," European Journal of Cardiothoracic surgery 12 (1997) pp. 406-412.

* cited by examiner

METHODS AND DEVICES FOR MINIMALLY INVASIVE CARDIAC SURGERY FOR ATRIAL FIBRILLATION

CROSS-REFERENCES TO RELATED APPLICATIONS

This application is a continuation of U.S. patent application Ser. No. 12/273,938, entitled "METHODS AND DEVICES FOR MINIMALLY INVASIVE CARDIAC SURGERY FOR ATRIAL FIBRILLATION," filed Nov. 19, 2008, which is a divisional of U.S. patent application Ser. No. 10/310,675, entitled "METHODS AND DEVICES FOR MINIMALLY INVASIVE CARDIAC SURGERY FOR ATRIAL FIBRILLATION," filed Dec. 4, 2002, which claims priority to U.S. Provisional Patent Application Ser. No. 60/337,070, entitled "METHODS AND DEVICES FOR THE LEAST INVASIVE CARDIAC SURGERY OF ATRIAL FIBRILLATION," filed Dec. 4, 2001, the entire contents of which is hereby incorporated by reference.

BACKGROUND OF THE INVENTION

The present invention relates generally to medical devices and methods. More specifically, the invention relates to devices and methods for enhancing minimally invasive cardiac surgery of atrial fibrillation.

Atrial fibrillation (AF) is a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3% of those aged 50-59 to more than 7% of those aged 80 and over. AF is responsible up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be underprescribed for AF. Despite the fact that warfarin reduces stroke risk by 60% or more, only 40% of patients age 65-74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

Although cardiac ablation devices and methods are currently available, many advances may still be made to provide improved devices and methods for ablating epicardial tissue to treat AF and other arrhythmias. For example, currently available devices can be difficult to position and secure on epicardial tissue to perform an ablation. Devices such as bipolar ablation clamps and others can ablate tissue only in very limited patterns, such as one or two straight lines. Ablation devices often have no means for shielding ablative energy, to avoid unwanted burning of tissues in the vicinity of the heart, such as the esophagus. Relatively few devices can be secured to epicardial tissue with sufficient force to allow for stabilization of the heart. And many ablation devices may not be introduced by minimally invasive means, thus requiring an open surgical procedure. Typically, therefore, current cardiac ablation procedures for AF treatment still require stopping the heart and using a cardiopulmonary bypass apparatus. Many of these shortcomings are addressed by devices and methods described in co-pending U.S. patent application Ser. No. 10/272,446, filed by the inventor of the present application on Oct. 15, 2002, the full disclosure of which is hereby incorporated by reference.

Another shortcoming in currently available surgical techniques is the difficulty of gaining optimal visualization of a surgical site on the heart and/or of structures in and around the surgical site. In other words, gaining sufficient visualization to allow the surgeon to accurately manipulate, ablate or otherwise operate on the heart is sometimes challenging using current methods and devices. Positioning a visualization device, for example between pericardial tissue and the outer surface of the heart, and maintaining the position of the device for visualizing an ablation procedure can often be difficult using currently available devices and techniques. Oftentimes, visualization devices and surgical instruments collide or simply overcrowd a surgical site, reducing a surgeon's room to work in and visualize the surgical site.

Therefore, a need exists for devices, systems and methods for enhancing minimally invasive cardiac surgery to treat AF and other cardiac arrhythmias. Preferably, such devices and methods would provide improved visualization of the heart and/or to an area around the heart where a surgical procedure is being performed. Also preferably, such visualization devices and methods would provide improved visualization without crowding the surgical site. Further, it would be desirable for such methods and devices to be minimally invasive. At least some of these objectives will be met by the present invention.

BRIEF SUMMARY OF THE INVENTION

The present invention generally provides improved methods, devices and systems for minimally invasive cardiac surgery, such as surgery to treat atrial fibrillation. In one aspect, a method for enhancing visualization of a surgical procedure on a heart of a patient comprises: introducing an elongate visualization device into the patient; advancing the visualization device to position at least one inflatable balloon on the visualization device between the heart and a layer of pericardium adjacent the heart; inflating the at least one inflatable balloon; and using the visualization device to visualize the heart during the surgical procedure. Introducing the visualization device may be accomplished through any suitable incision, such as a subzyphoid incision, a subcostal incision or a thoracotomy. Advancing the visualization device may include advancing the device through the layer of pericardium. Inflating at least one balloon may include inflating one balloon disposed around a circumference of the visualization device. In another embodiment, inflating at least one balloon comprises inflating at least two balloons disposed around a circumference of the visualization device, wherein one balloon is located between the heart and the layer of pericardium and the other balloon is located proximal to the pericardium.

In some embodiments, the method further includes protecting an optical element of the visualization device by using the balloon to reduce contact of the optical element with other structures. Some embodiments may also include cleaning the optical element by introducing a fluid through a lumen in the visualization device to contact the optical element. A method may further include introducing an ablation device through a first lumen in the visualization device to contact the heart. Additionally, in some embodiments, the method includes introducing at least one of a clamp, a positioning device, a stabilization device, a cutting device, a cardiac mapping device, a catheter, a left atrial appendage clip applier, an insufflation device and an irrigation device through at least a second lumen in the visualization device. The method may also include: ablating the heart, using the ablation device; removing the ablation device from the first lumen; introducing a left atrial appendage clip applier through the first lumen to contact a left atrial appendage of the heart; and applying at least one clip to the left atrial appendage. In some embodiments, the method also includes providing light to the visualization device from a control unit; and providing ablation energy to the ablation device from the control unit. Optionally, the method may include providing at least one of insufflation and irrigation to the visualization device from the control unit. Also optionally, the method may comprise recording at least one image acquired by the visualization device on the control unit.

In another aspect, a visualization device for enhancing minimally invasive heart surgery comprises an elongate visualization member having a proximal end and a distal end and at least one inflatable balloon coupled with the visualization member at or near the distal end. In some embodiments, for example the visualization member comprises an endoscope. Alternatively, the visualization member is selected from the group consisting of an ultrasound device, a fluoroscopy device, an MRI device and a stereotactic positioning device. In some embodiments, the proximal end of the visualization member is removably couplable with an image viewing device. In many embodiments, the device further includes means for inflating the at least one inflatable balloon. For example, the means for inflating may include an infusion lumen for infusing at least one of air or a fluid into the at least one inflatable balloon. The at least one balloon may comprise a first balloon disposed around a circumference of the visualization device such that when the first balloon is inflated it creates a space between a pericardial layer around a heart and an outer surface of the heart. Optionally, the at least one balloon may further comprise a second balloon disposed around the circumference of the visualization device at a location proximal to the first balloon. In some embodiments, the first balloon, when inflated, at least partially protects an optical element of the visualization device from harm due to contact.

In some embodiments, the visualization device also includes a first lumen for allowing passage of an ablation device. Optionally, the device may include at least a second lumen for allowing passage of at least one of a clamp, a positioning device, a stabilization device, a cutting device, a cardiac mapping device, a catheter, a left atrial appendage clip applier, an insufflation device and an irrigation device. In some embodiments, the device includes an irrigation lumen for introducing a cleaning fluid to contact and clean an optical element of the visualization device.

In yet another aspect, a clip applier for applying at least one clip to a left atrial appendage of a heart of a patient comprises: an elongate shaft defining a proximal end and a distal end; clip applying means coupled with the shaft at or near the distal end; and an actuator coupled with the shaft at or near the distal end and also coupled with the clip applying means so as to actuate the applying means to apply the at least one clip to the left atrial appendage. In some embodiments, the device is introducible through a lumen of a visualization device. Optionally, the clip applier may further include at least one clip coupled with the device in a position to allow the clip applying means to apply the clip to the atrial appendage. In some embodiments, the at least one clip does not sever the atrial appendage when applied to the appendage by the clip applying means.

In still another aspect, a system for performing an ablation procedure on a heart of a patient comprises: a visualization device comprising an elongate visualization member having a proximal end and a distal end and at least one inflatable balloon coupled with the visualization member at or near the distal end; and an ablation device for ablating a portion of the heart. The visualization member, for example, may comprise an endoscope. In other embodiments, the visualization member is selected from the group consisting of an ultrasound device, a fluoroscopy device, an MRI device and a stereotactic positioning device. In some embodiments, the proximal end of the visualization member is removably couplable with an image viewing device. In all other aspects, the visualization device may have any of the features described above or any other suitable features.

In some embodiments, the system further includes a left atrial appendage clip applier for applying at least one clip to the left atrial appendage to reduce or stop blood flow through the appendage. Also optionally, the system may include a heart positioning device for moving the heart into a desired position. For example, the heart positioning device may include an elongate shaft defining a proximal end and a distal end and an inflatable positioning member coupled with the shaft at or near the distal end. The inflatable positioning member, for example, may be coupled with the shaft via a flexible joint selected from the group consisting of a ball and socket joint and a ball and collet joint. In other embodiments, the system includes at least one retractor device for facilitating introduction of the visualization device. Optionally, the at least one retractor device includes at least one retractor blade having a cushioned surface for reducing damage to a nerve when the cushioned surface contacts the nerve. For example, the nerve may be an intercostal nerve when the retractor device retracts a rib of a patient.

In some embodiments, the further comprises a control unit for coupling with at least the visualization device and the ablation device. The control unit may comprise, for example, a light source for providing light to the visualization device and an ablative energy source for providing ablative energy to the ablation device. In some embodiments, the control unit further comprises: a video source for coupling with the visualization device; at least one of an insufflation source and an irrigation source for providing insufflation and/or irrigation to the visualization device; and a power cord for connecting the control unit with a power source. Even further, the control unit may comprise an image recorder for recording images from the visualization device. In some embodiments, the ablative energy source of the control unit provides at least one of RF energy, cryogenic energy and microwave energy.

In another aspect, a control unit for enhancing a minimally invasive surgical procedure on a heart of a patient comprises a light source for providing light to the visualization device and an ablative energy source for providing ablative energy to the ablation device. As mentioned above, the control unit may further comprise a video source for coupling with the visualization device; at least one of an insufflation source and an irrigation source for providing insufflation and/or irrigation to the visualization device; and a power cord for connecting the control unit with a power source. Any other suitable feature may be included.

DETAILED DESCRIPTION OF THE INVENTION

Devices, systems and methods of the present invention provide for enhancement of heart surgery procedures. Generally, the invention provides for enhanced visualization of a surgical site on, around or near a patient's heart via the use of one or more devices. Various embodiments also provide additional features, such as improved access to the surgical site, prevention of clot dispersal from the left atrial appendage, improved heart positioning and stabilization and/or the like. The invention may be used to enhance any of a number of minimally invasive cardiac surgery procedures, such as ablation procedures for treating atrial fibrillation and the like. Thus, although the description below generally relates to ablation procedures for treating atrial fibrillation, any other suitable procedure may incorporate methods, devices and/or systems of the present invention. Various embodiments of the invention may be used in procedures involving a stopped heart and cardiopulmonary bypass, partial bypass, or in beating heart procedures.

Figure 1:
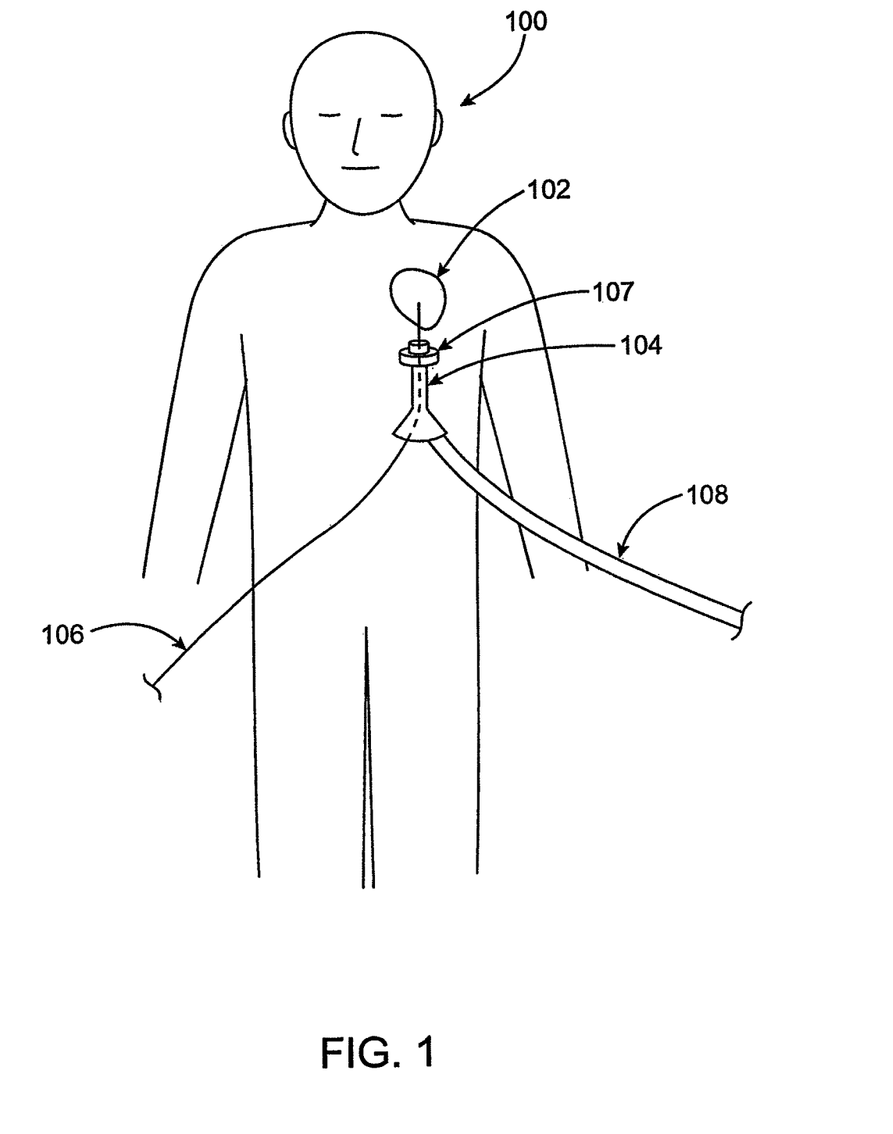
FIG. 1 is a schematic representation of a patient, showing a single-entry device for performing and viewing a cardiac surgery procedure, according to one embodiment of the present invention.

Referring now to FIG. 1, a schematic view of a patient 100 is shown, with a representation of a heart 102 and a visualization device 104 in position to visualize a portion of heart 102. Generally, visualization device 104 may comprise any suitable device for enhancing visualization of a surgical field and/or heart 102. For example, in some embodiments visualization device 104 comprises an endoscope, such as commercially available endoscopes or endoscopes developed in the future. Such endoscopes may be flexible, rigid, or partially flexible and partially rigid. In other embodiments, any other suitable visualization devices may be used, such as ultrasound devices, fluoroscopic devices, MRI devices, stereotactic positioning devices or the like. In some embodiments, visualization device includes at least one inflatable balloon 107 at or near its distal end. As will be described further below, balloon 107 may enhance visualization with visualization device 104, protect optical elements of the device 104, help maintain a position of the device 104 and/or perform other functions. Typically, visualization device 104 is coupled at or near its proximal end with a control unit (not shown), for example a unit including a light source, via a connector 108. It will be understood by those skilled in the art that multiple connectors 108 may be used to couple visualization device 104 to one or more control units for multiple purposes. For example, separate connectors 108 may be used for coupling with a light source, a source of insufflation, a source of irrigation, a video monitor or other image capture device and/or the like.

In some embodiments, one or more additional devices may be introduced into patient 100 via visualization device 104. For example, in one embodiment an ablation device 106 for ablating a pattern on heart 102 for treating atrial fibrillation may be introduced via visualization device 104. Often, additional devices such as ablation device 106 are introduced through one or more lumens on visualization device 104. Ablation device 106 may be any suitable ablation device, such as a radio frequency (RF) device or the like. In some embodiments, ablation device may comprise one or more of the devices described in U.S. patent application Ser. No. 10/272,446, previously incorporated by reference. Ablation device 106 is typically connected, at or near its proximal end, to a controller device (not shown), for activating an ablation member and the like. As described further below, any suitable combination of instruments, devices and the like may be introduced through access device 104.

Visualization device 104 may be introduced into patient 100 via a primary incision placed in any suitable location. For example, in one embodiment the primary incision comprises a subzyphoid incision, but in other embodiments a subcostal incision, an intercostal incision or any other suitable incision may be used.

Figure 2:
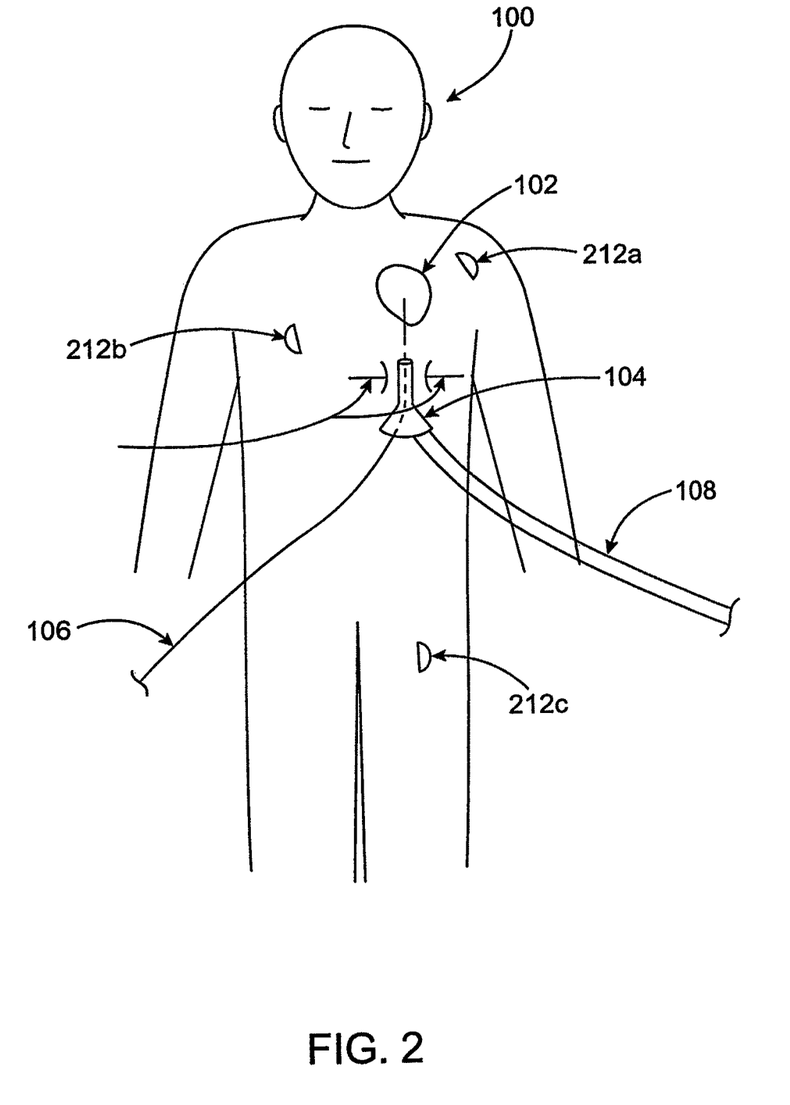
FIG. 2 is a schematic representation of a patient, showing a multiple-entry device for performing and viewing a cardiac surgery procedure, according to one embodiment of the present invention.

Referring now to FIG. 2, in some surgical procedures, additional devices may be used and additional incisions may be made on patient 100. Generally, visualization device 104 of FIGS. 1 and 2 may be introduced into the patient and advanced to the surgical site via any suitable incision, as described above. To facilitate introduction of visualization device 104, one or more retractors 210 may be used to increase the size of an incision. One or more additional incisions on patient 100 may include, for example, an arterial/venous access incision 212a for providing access for a perfusion cannula to a cardiopulmonary bypass machine or for any other device, an incision for a separately-introduced left atrial appendage clamp or clip 212b, and/or a femoral incision 212c for providing access to a femoral artery for entry of a mapping catheter or any other device. Any suitable combination of incisions 212 and devices is contemplated within the scope of the invention.

Figure 3A:
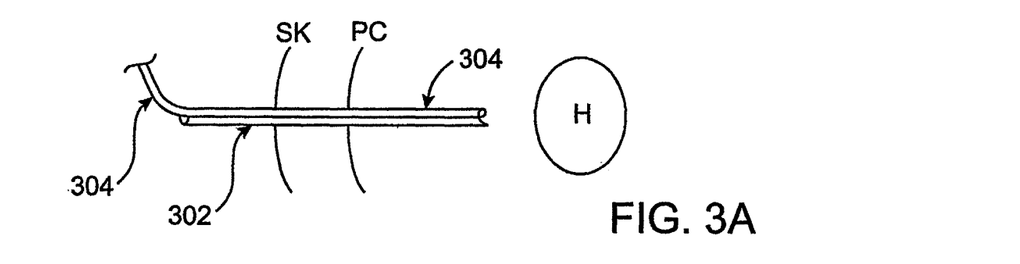
FIG. 3A is a schematic side view of a visualization device for viewing a heart, according to one embodiment of the present invention.
Figure 3B:
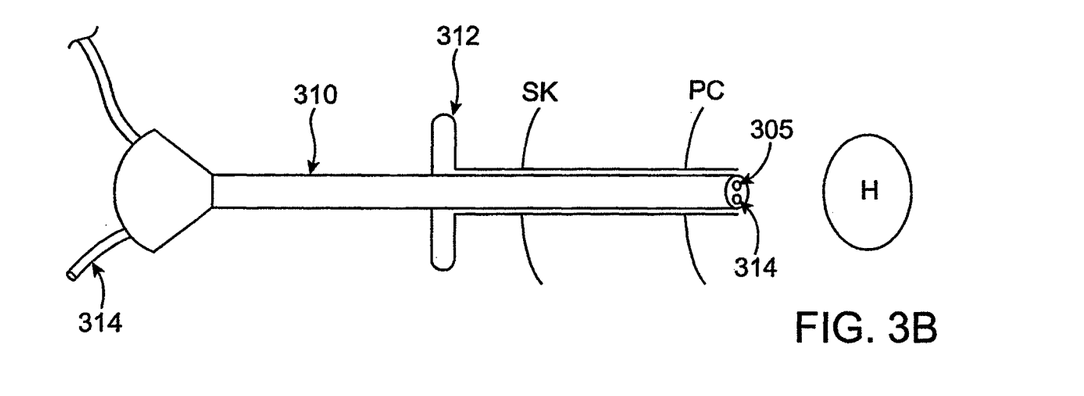
FIG. 3B is a schematic side view of a visualization device for viewing a heart, according to another embodiment of the present invention.
Figure 3C:
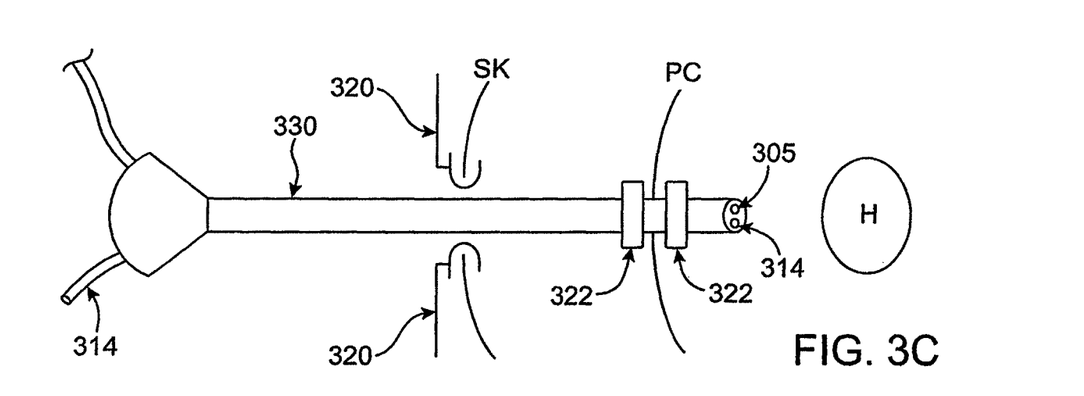
FIG. 3C is a schematic side view of a visualization device having two inflatable balloons, according to another embodiment of the present invention.

Referring now to FIGS. 3A-3C, several different types of visualization devices are shown, each in relation to skin (SK), pericardium (PC) and a heart (H) of a patient (none of which are drawn to scale.) In one embodiment, with reference to FIG. 3A, a visualization device 304 is coupled with an insertion needle 302, which comprises a thin, elongate needle-like device or sheath-like device for aiding delivery of visualization device 304 to a desired location. Insertion needle 302 is typically a small-profile device, perhaps between 1-3 mm, to allow for minimally invasive introduction of visualization device 304. FIG. 3B shows a visualization device 310 configured for introduction through a trocar 312 or other, similar introducer sheath or device. In some embodiments, visualization device 310 includes both a visualization member 305 and one or more lumens 314 for allowing introduction of ablation devices or the like.

As shown in FIG. 3C, another embodiment of a visualization device 330 may be used in conjunction with one or more retractors 320 for facilitating entry of visualization device 330 into the patient. Retractors 320 may comprise any suitable retractor devices. In one embodiment, retractors 320 include one or more hinges to help retractors 320 conform to a body surface. In another embodiment, retractor blades include a pliant, cushioning or otherwise trauma-reducing surface for reducing damage to a nerve with which retractor 320 comes in contact. Any suitable retractors 320 and retractor blades are contemplated. In some embodiments, visualization device 330 also includes one or more inflatable balloons 322 disposed along it outer surface. Inflatable balloons 322 are typically located at or near the distal end of visualization device 303, such that when inflatable balloons 322 are inflated at least one balloon 322 is located between heart H and pericardium PC. Balloon 322 may thus create a space between heart H and pericardium PC to facilitate visualization of heart H. One or more balloons 322 may also partially or completely cover visualization member 305 to protect one or more optical elements of the member 305. In some embodiments, balloon(s) 322 also help maintain visualization device in a desired location. Generally, inflatable balloons 322 may have any desired configuration and may be inflated via any suitable means, such as by an inflation lumen in visualization device 330 coupled with a source of air or other inflation medium.

Figure 3D:
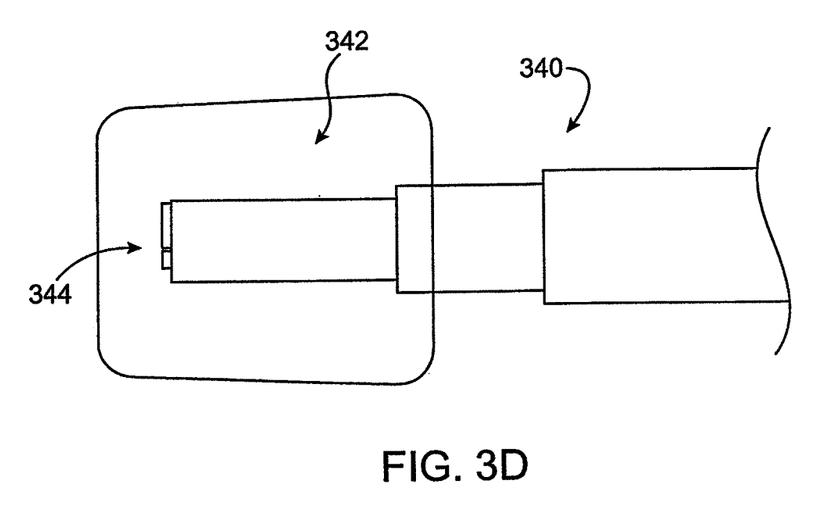
FIG. 3D is a side view of a visualization device having an inflatable balloon, according to another embodiment of the present invention.
Figure 3E:
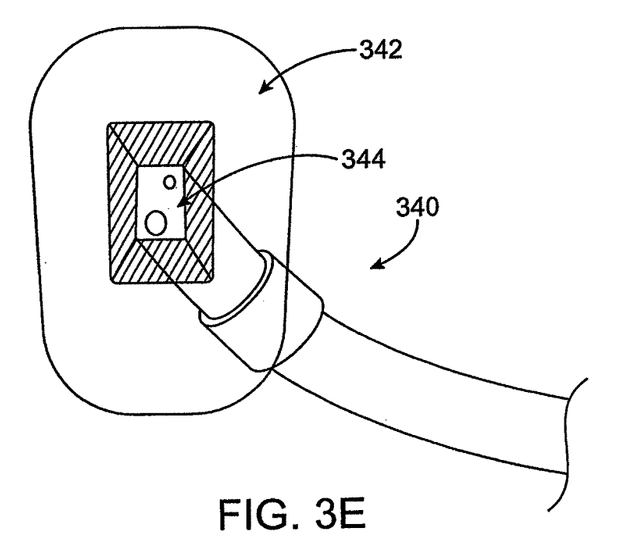
FIG. 3E is a perspective view of the visualization device in FIG. 3D.

Referring now to FIGS. 3D and 3E, a side view and a perspective view of a distal end of a visualization device 340 with an inflatable balloon 342 are shown, respectively. As can be seen from these views, balloon 342 may be configured to cover or otherwise protect an optical element 344 of visualization device 340. In this example, optical elements 344 are recessed from the distal end of balloon 342, as shown by the shaded surface in FIG. 3E. As should be understood by those skilled in the art, any other configuration of inflatable balloon 342, or any combination of balloons, may be used without departing from the scope of the invention.

Figure 4:
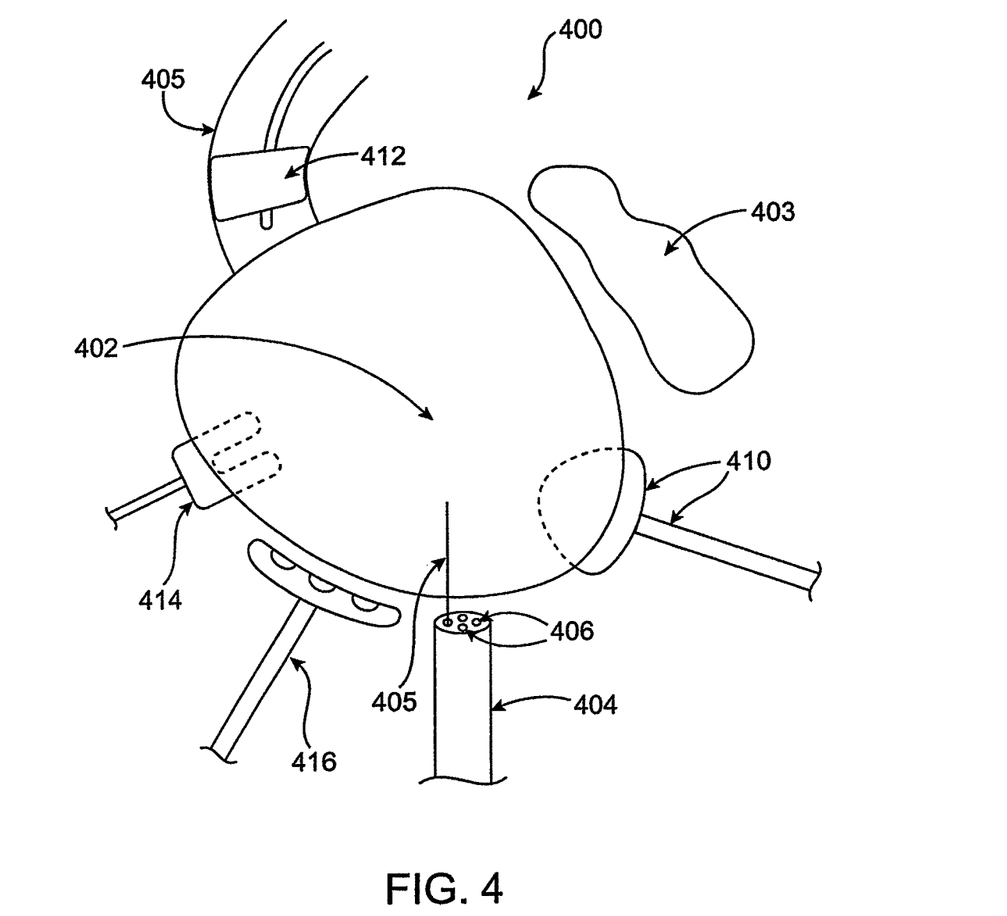
FIG. 4 is an inferior/bottom-side view of a heart, showing multiple devices which may be used to provide access, positioning and visualization of the heart, according to one embodiment of the present invention.

With reference now to FIG. 4, a schematic representation of a surgical site is shown from the perspective of an inferior heart surface 402. A surgical system 400 for performing heart surgery according to the present invention may include multiple devices. Typically, at least one visualization device 404 will be used, in some embodiments having one or more lumens 406 for introducing one or more additional devices to the surgical site. Thus, additional devices may be introduced through lumen(s) in visualization device 404, but they may alternatively be introduced through separate incisions, or through both visualization device 404 and separate incisions. For example, an ablation device 405 may be introduced through visualization device 404, as described above. Other devices may be introduced either separately or through visualization device. Such devices include a device for deflating the left lung 403 (device not shown) to allow greater access to and visibility of the heart 402. Additionally, one or more catheters 412 may be used to decompress the heart 402, for example by partially or completely blocking one or more blood vessels such as the aorta 405. An inflatable positioning device 410 may be used to position the heart 402, a heart retractor 414 may be further used to position the heart 414, and one or more stabilizers 416 may be used to maintain a position of the heart.

It should be understood, from FIG. 4, that any suitable combination of devices, introduced into a patient via any suitable combination of minimally invasive incisions, is contemplated within the scope of the present invention. One embodiment, for example, may employ one or more ablation devices described in U.S. patent application Ser. No. 10/272,446, previously incorporated by reference. Some embodiments may use retractors as described in U.S. Pat. No. 6,309,349, entitled "Surgical Retractor and Stabilizing Device and Method for Use," the entire disclosure of which is hereby incorporated by reference. Any other suitable devices may be used along with visualization device 404 to enhance minimally invasive surgery on the heart 402 via surgical system 400.

Figure 5A:
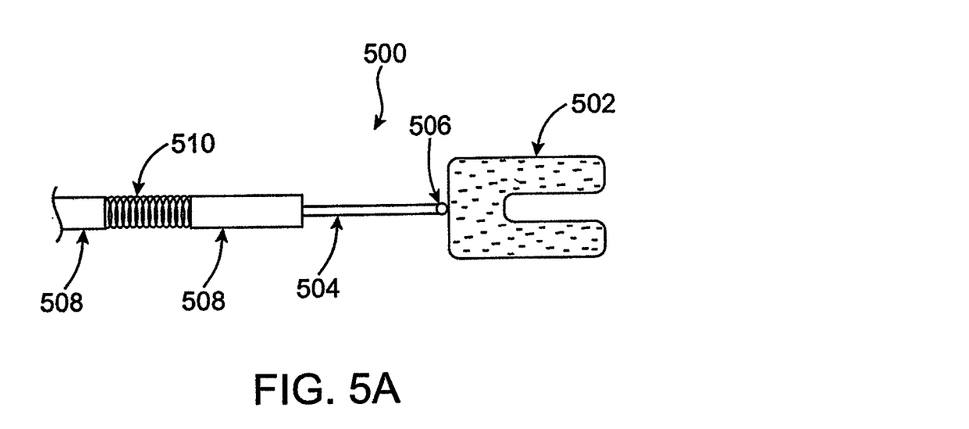
FIG. 5A is a perspective view of a heart retractor, according to one embodiment of the present invention.

Referring now to FIG. 5A, one of the devices in surgical system 400 may include a heart retractor 500. Heart retractor 500 suitably includes a retracting surface 502 coupled with an elongate shaft 540 via a flexible connector 506 such as a ball and socket joint or ball and collet joint. Elongate shaft 540 may be coupled at its proximal end with a rapid disconnect coupling mechanism 508. Rapid disconnect 508 may, in turn, comprise a flexible segment 510 for enhancing maneuverability. In one embodiment, rapid disconnect 508 may be coupled, at its proximal end, with a stable structure, such as an arm of an operating table, to maintain the position of the heart retractor 500.

Figure 5B:
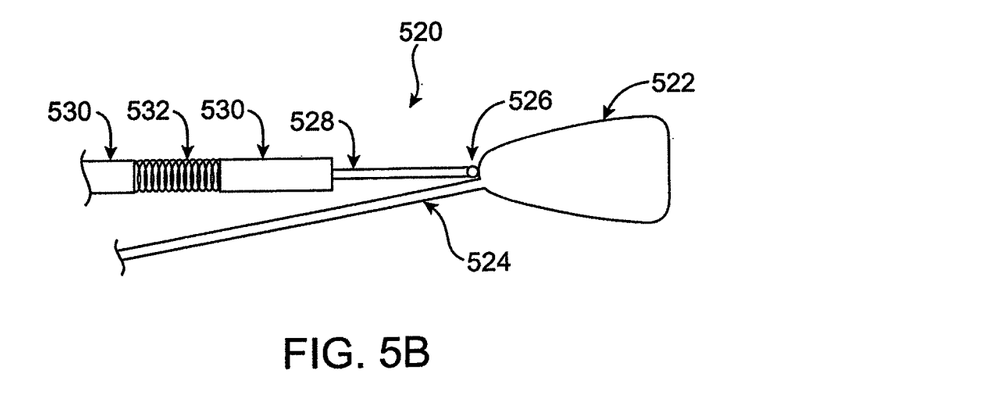
FIG. 5B is a perspective view of a heart retractor, according to another embodiment of the present invention.

With reference to FIG. 5B, another device which may be used with surgical system 400 comprises an inflatable heart retractor 520 or "pillow retractor." Inflatable retractor 520 comprises an inflatable retractor surface 522, coupled with an elongate shaft 528 via a flexible connector 526. Again, shaft 528 is coupled with a rapid disconnect 530, which may or may not include a flexible segment 532. Inflatable retractor 520 also includes means for inflating the retractor surface 522, which may comprise, for example, an inflation cannula 524 within or outside of elongate shaft 528. Inflatable heart retractor 520 may be particularly advantageous in positioning the heart by placing the inflatable surface 522 in contact with a posterior portion of the heart and inflating the surface 522 to move the heart in an anterior direction—i.e., closer to the surgeon. Creating a space behind the heart may be very advantageous in visualizing the back of the heart and/or in maneuvering one or more surgical devices to operate on the back of the heart.

Figure 5C:
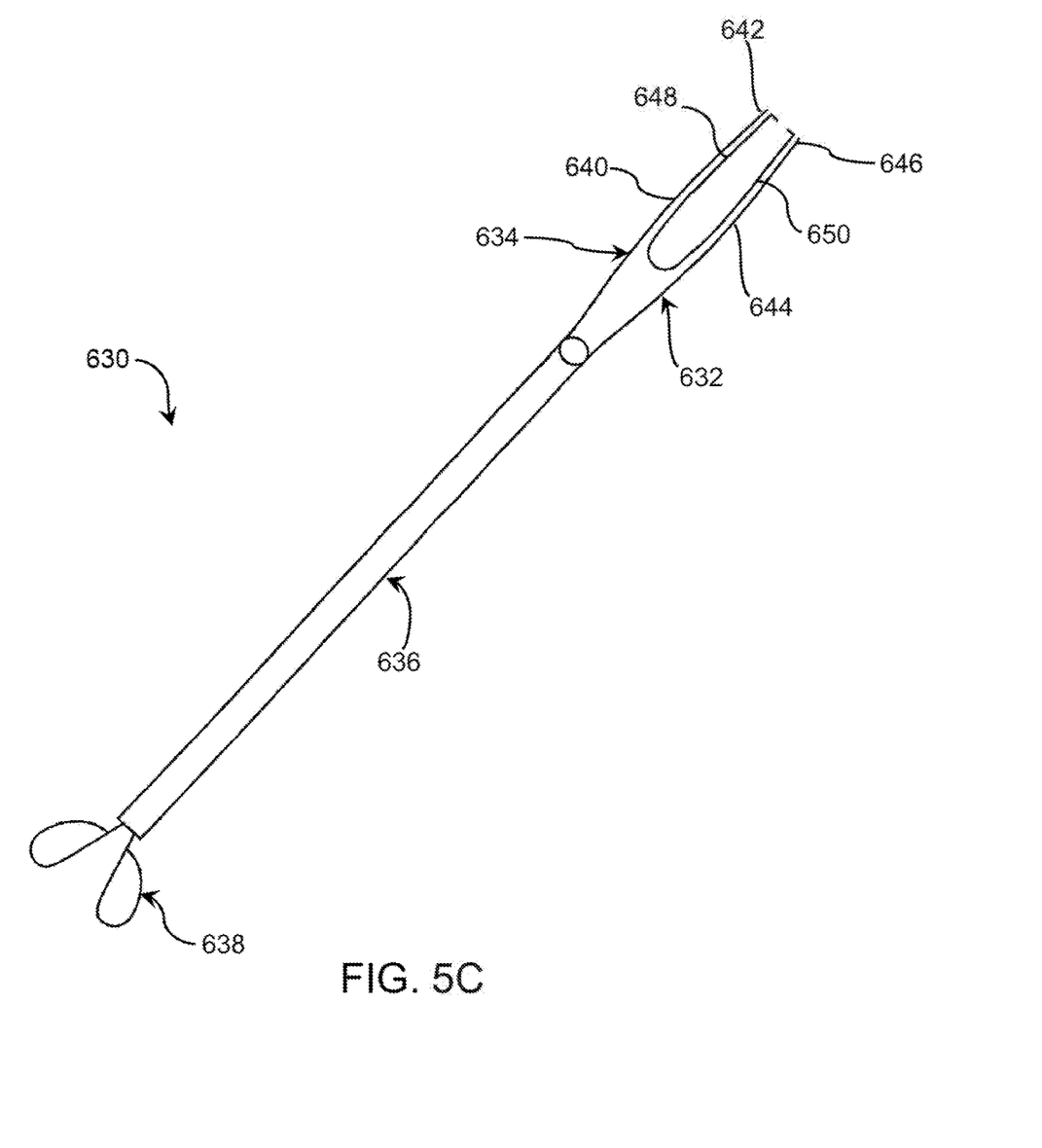
FIG. 5C is a perspective view of a left atrial appendage clip applying device, according to an embodiment of the present invention.

With reference now to FIG. 5C, one device which may be introduced via a visualization device of the invention or via a separate incision on a patient comprises a left atrial appendage clip applier 630 having a first elongate applier member 640 with a first applier distal end 642 and a second elongate applier member 644 with a second applier distal end 646. Clip applier 630 is typically used to apply one or more clips to the left atrial appendage of the heart to prevent clots from the left atrial appendage from embolizing and causing harm to the patient, such as a stroke. Clip applier 630 suitably includes a clamp 632 or other means for applying a clip 634, coupled with an elongate shaft 636, which in turn is coupled with a handle 638 for operating the clamp 632. The clamp 632 includes a first elongate segregation member 648 and a second elongate segregation member 650. Clip applier 630 will generally have a shape and profile which will allow it to be introduced either through a visualization device of the present invention or via a separate incision. Clips 634 are typically configured to segregate the left atrial appendage without severing the appendage, but otherwise any suitable configuration is contemplated, such as a U-shaped clip or the like. In one embodiment, clip applier 630 may be used to simultaneously clip and excise the atrial appendage.

Figure 6A:
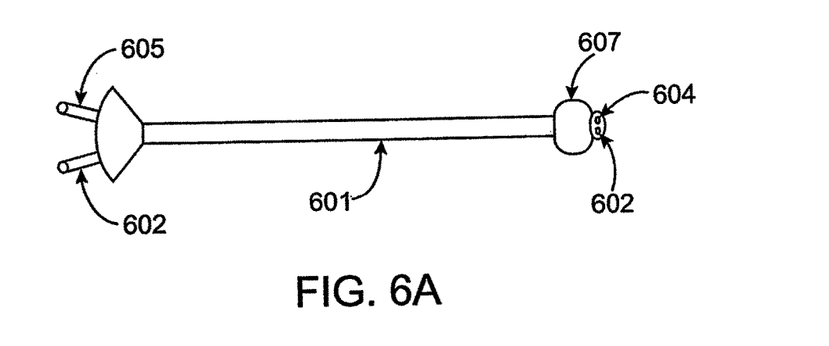
FIG. 6A is a perspective view of a viewing device providing means for introducing an ablating device, according to one embodiment of the present invention.

Referring now to FIG. 6A, another embodiment of a visualization device 601 is shown. Again, as has been described above, viewing device comprises often a scope, such as an endoscope, and includes an optical or visualization element 604 and one or more connectors 605 for connecting to a light source and/or other devices. Visualization device 601 also includes at least one inflatable balloon 607, as discussed above, for enhancing visualization and/or for protecting optical element 604. In many embodiments, visualization device 601 also includes one or more lumens for allowing introduction of an ablation device or any other suitable device(s). In some embodiments, such as the embodiment in FIG. 6A with one lumen, the profile of visualization device 601 may be quite small. For example, the device 601 may have an outer diameter of between about 1 mm and about 3 mm.

Figure 6B:
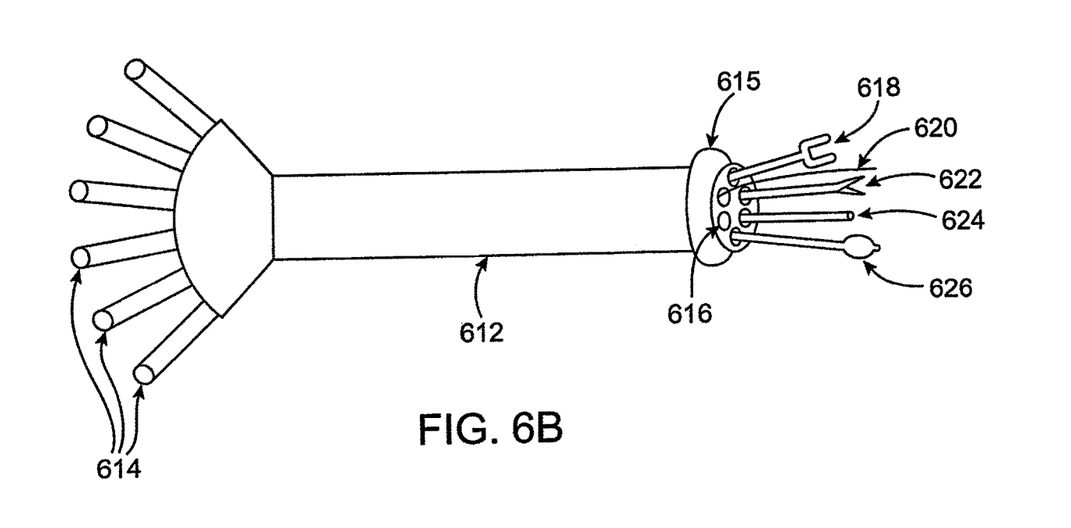
FIG. 6B is a perspective view of a viewing device providing means for introducing multiple devices, according to one embodiment of the present invention.

In another embodiment, as shown in FIG. 6B, a visualization device 612 may have multiple lumens 614 for allowing introduction of multiple devices. Again, a balloon 615 and an optical element 616 will be included. Multiple lumens 614 may provide means for passage, for example, of a clamp 618 or positioning device, an ablation device 620, cutting apparatus 622, an irrigation or insufflation cannula 624, a mapping catheter 626, or any other suitable device.

Figure 7:
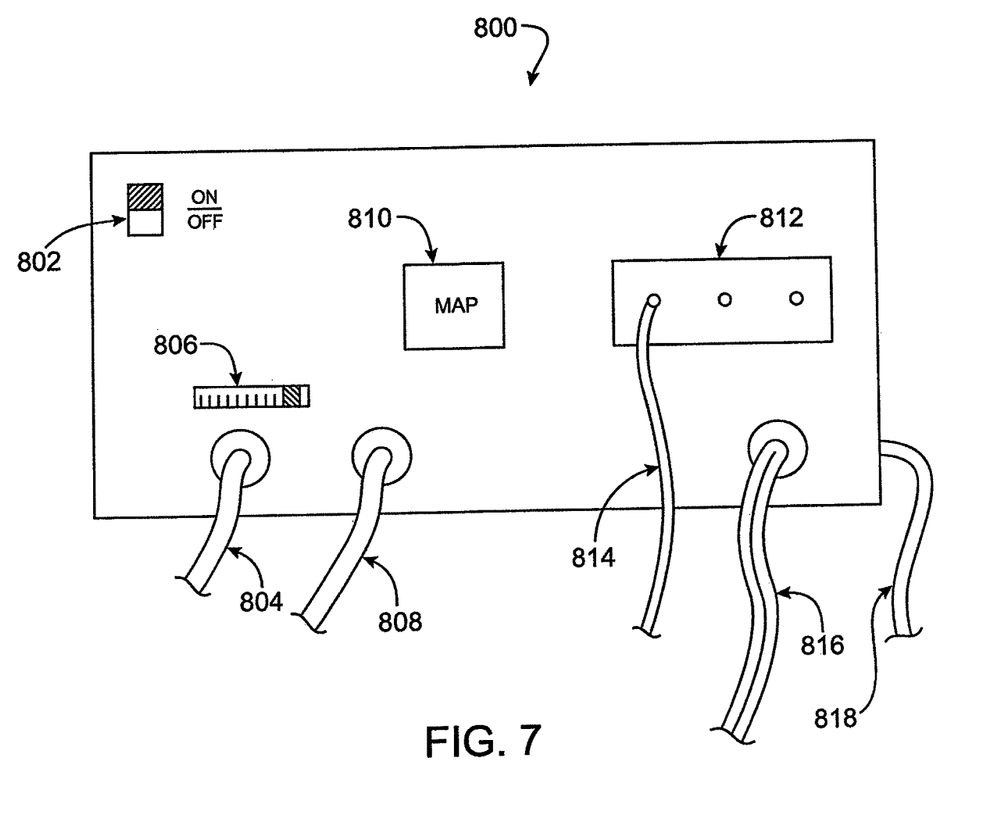
FIG. 7 is a frontal, schematic view of a control unit for a minimally invasive surgical system, according to one embodiment of the present invention.

Finally, with reference now to FIG. 7, many of the devices in surgical system 400 described above may be coupled with a common control unit 800. Control unit 800, for example, may include a power switch 802, an outlet for a light cable 804, a light intensity meter 806, an outlet for a video cable 808, an electrical signal mapping component 810, an ablation source outlet 812 for connecting to an ablation device 814, an insufflation/irrigation outlet for coupling with an insufflation/irrigation cannula 816 and a power cord 818 for coupling control unit 800 with an external power source. Thus, a visualization device, for example, may be coupled with control unit 800 via video cable 808 and light cable 804, an ablation device 814 may be coupled with control unit 812 to receive ablative energy, such as RF energy, and multiple other devices and functions may be controlled via control unit. It will be understood by those skilled in the art that other devices and functions, such as any of the devices described above or any other suitable devices, may be coupled with control unit 800 in various embodiments.

Although the invention has been fully described above, in relation to various exemplary embodiments, various additions or other changes may be made to the described embodiments without departing from the scope of the present invention. Thus, the foregoing description has been provided for exemplary purposes only and should not be interpreted to limit the scope of the invention as set forth in the following claims.

What is claimed is:

1. A method of occluding a left atrial appendage of a heart of a patient, comprising:
   introducing an applier into the patient via a first incision, the applier having an elongate shaft defining a proximal end and a distal end and an applier device coupled with the elongate shaft at or near the distal end, the applier device carrying an atrial segregation device separable from the applier device, the applier device having a first elongate applier member with a first applier distal end and a second elongate applier member with a second applier distal end, and the atrial segregation device having a first elongate segregation member and a second elongate segregation member, where the first elongate applier member is parallel to a middle portion of the first elongate segregation member and the second elongate applier member is parallel to a middle portion of the second elongate segregation member, wherein the first and second applier distal ends terminate along outer lateral sides of the first and second elongate segregation members and a distal portion of the applier device co-terminates with a distal portion of the atrial segregation device;

visualizing a portion of the heart by introducing a visualization device into the patient via a second incision, where the second incision is one of a subxiphoid incision, a subcostal incision, and a thoracotomy;

introducing an ablation device through a lumen of the visualization device, the ablation device configured to ablate tissue;

segregating the left atrial appendage by applying the atrial segregation device to the left atrial appendage of the heart with the applier device such that the left atrial appendage is positioned between the first and second elongate applier members and between the first and second elongate segregation members; and actuating the applier device to move the first and second elongate applier members to compress the first and second elongate segregation members such that the first and second elongate segregation members compress the left atrial appendage without severing the appendage.

2. The method according to claim 1, wherein the atrial segregation device comprises a clip disposed within the applier device.

3. The method according to claim 1, wherein the atrial segregation device comprises a clamp disposed within the applier device.

4. The method according to claim 1, further comprising providing insufflation to the introduction means from an insufflation source.

5. The method according to claim 1, wherein the applier device holds the atrial segregation device as a U-shaped configuration.

6. The method according to claim 1, wherein the atrial segregation device is disposed within the applier device.

7. The method according to claim 1, wherein the applier further comprises a handle for operating the applier device.

8. The method according to claim 1, wherein the method comprises clipping and excising the left atrial appendage.

9. The method according to claim 1, further comprising contacting the left atrial appendage with the applier.

10. The method according to claim 1, further comprising:
separating the applier device from the atrial segregation device after applying the atrial segregation device to the left atrial appendage.

11. The method according to claim 1, further comprising:
leaving the atrial segregation device applied to the left atrial appendage while the first incision is closed.

12. A method of occluding a left atrial appendage of a heart of a patient, comprising:
introducing an applier having a left atrial appendage device into the patient via a first incision, the left atrial appendage device being separable from the applier, the applier having a first elongate applier member with a first applier distal end and a second elongate applier member with a second applier distal end, and the left atrial appendage device having a first elongate appendage member and a second elongate appendage member where the first elongate applier member is parallel to a middle portion of the first elongate appendage member and the second elongate applier member is parallel to a middle portion of the second elongate appendage member, wherein the first and second applier distal ends terminate along outer lateral sides of the first and second elongate appendage members and a distal portion of the applier co-terminates with a distal portion of the left atrial appendage device;

visualizing a portion of the heart by introducing a visualization device into the patient via a second incision, where the second incision is one of a subxiphoid incision, a subcostal incision, and a thoracotomy, introducing an ablation device through a lumen of the visualization device, the ablation device configured to ablate tissue;

introducing a mapping catheter through the lumen of the visualization device, the mapping catheter configured to follow a path of the ablation device;

segregating the left atrial appendage by applying the left atrial appendage device to the left atrial appendage of the patient with the applier such that the left atrial appendage is positioned between the first and second elongate appendage members of and between the first and second elongate applier members; and actuating the applier device so that the first and second elongate applier members compress the first and second elongate appendage members, compressing the left atrial appendage.

13. The method according to claim 12, further comprising introducing an insufflation device into the patient.

14. The method according to claim 13, wherein the insufflation device is introduced into the patient via the elongate visualization device.

15. The method according to claim 12, wherein the visualization device comprises a visualization member, the method further comprising advancing the visualization device to position at least one inflatable balloon on the visualization device between the heart and a layer of pericardium adjacent the heart and to position the visualization member of the visualization device between the heart and the layer of pericardium.

16. The method according to claim 15, further comprising inflating the at least one inflatable balloon while the at least one inflatable balloon is disposed between the heart and the layer of pericardium so as to create a space between the heart and the layer of pericardium.

17. The method according to claim 16, further comprising using the visualization member of the visualization device to visualize the heart during the surgical procedure while the visualization member is disposed in the space between the heart and the layer of pericardium created by the at least one inflatable balloon.

18. The method according to claim 16, wherein the step of inflating the at least one inflatable balloon comprises inflating one balloon disposed around a circumference of the visualization device.

19. The method according to claim 12, further comprising:
leaving the left atrial appendage device applied to the left atrial appendage while the first incision is closed.

* * * * *